(12) United States Patent
Felding et al.

(10) Patent No.: US 12,337,094 B2
(45) Date of Patent: Jun. 24, 2025

(54) METHOD FOR DETECTION OF FLOW OBSTRUCTION IN AN EXTRACORPOREAL CIRCUIT, APPARATUS AND COMPUTER PROGRAM

(71) Applicant: GAMBRO LUNDIA AB, Lund (SE)

(72) Inventors: Anders Felding, Malmö (SE); Peter Marklund, Lund (SE); Anders Sneckenborg, Ängelholm (SE)

(73) Assignee: Gambro Lundia AB, Lund (SE)

( * ) Notice: Subject to any disclaimer, the term of this patent is extended or adjusted under 35 U.S.C. 154(b) by 592 days.

(21) Appl. No.: 17/267,405

(22) PCT Filed: Jul. 31, 2019

(86) PCT No.: PCT/EP2019/070582
§ 371 (c)(1),
(2) Date: Feb. 9, 2021

(87) PCT Pub. No.: WO2020/030486
PCT Pub. Date: Feb. 13, 2020

(65) Prior Publication Data
US 2021/0299342 A1    Sep. 30, 2021

(30) Foreign Application Priority Data
Aug. 9, 2018  (SE) .................................. 1850967-9

(51) Int. Cl.
*A61M 1/36*    (2006.01)
*A61M 1/34*    (2006.01)

(52) U.S. Cl.
CPC ........ *A61M 1/3639* (2013.01); *A61M 1/3417* (2014.02); *A61M 1/3624* (2013.01);
(Continued)

(58) Field of Classification Search
CPC .............. A61M 1/3639; A61M 1/3417; A61M 1/3624; A61M 1/3627; A61M 1/3663;
(Continued)

(56) References Cited

U.S. PATENT DOCUMENTS 4,469,593 A * 9/1984 Ishihara .............. A61M 1/3427
                                                    210/104
5,096,385 A   3/1992 Georgi et al.
(Continued)

FOREIGN PATENT DOCUMENTS

JP    2005532099 A * 5/2003 .............. A61M 1/16

OTHER PUBLICATIONS

Swedish Search Report from corresponding Swedish Patent Application No. 1850967-9, mailed Feb. 7, 2019.
(Continued)

*Primary Examiner* — Rebecca E Eisenberg
*Assistant Examiner* — Matthew Wrubleski
(74) *Attorney, Agent, or Firm* — K&L Gates LLP (57) ABSTRACT

An extracorporeal circulation blood or treatment device (100) comprising an arterial pressure sensor (112) and a blood pump (111) is set up to determine amplitude variation and frequency of the pressure signals received from said arterial pressure sensor (112), calculate a parameter value based on said amplitude variation and said frequency, and issue an alarm if the parameter value exceeds a pre-set threshold value. Such detection aims at monitoring the occurrence of oscillating pressure signals. Such signals indicate an increased risk for hemolysis.

10 Claims, 5 Drawing Sheets

(52) U.S. Cl.
CPC ........ *A61M 1/3627* (2013.01); *A61M 1/3663* (2013.01); *A61M 2205/18* (2013.01); *A61M 2205/3331* (2013.01); *A61M 2205/3389* (2013.01)

(58) Field of Classification Search
CPC .............. A61M 1/367; A61M 2205/18; A61M 2205/3331; A61M 2205/3389
See application file for complete search history.

(56) References Cited

U.S. PATENT DOCUMENTS

| | | | |
|---|---|---|---|
| 5,906,589 | A | 5/1999 | Gordon et al. |
| 6,623,443 | B1 | 9/2003 | Polaschegg |
| 7,632,411 | B2 | 12/2009 | Kuroda et al. |
| 9,216,248 | B2 | 12/2015 | Suffritti et al. |
| 9,289,545 | B2 * | 3/2016 | Olde .................. A61M 1/3659 |
| 9,612,182 | B2 | 4/2017 | Olde et al. |
| 10,195,326 | B2 | 2/2019 | Fulkerson et al. |
| 2002/0174721 | A1 | 11/2002 | Gross |
| 2009/0149795 | A1 | 6/2009 | O'Mahony et al. |
| 2009/0177148 | A1 * | 7/2009 | DelCastillo ....... A61M 5/16831 604/67 |
| 2013/0211730 | A1 | 8/2013 | Wolff |
| 2016/0296686 | A1 | 10/2016 | Ritter et al. |
| 2017/0319771 | A1 | 11/2017 | Vasta et al. |

OTHER PUBLICATIONS

International Search Report from corresponding International Patent Application No. PCT/EP2019/070582, mailed Oct. 29, 2019.
Written Opinion from corresponding International Patent Application No. PCT/EP2019/070582, mailed Oct. 29, 2019.

* cited by examiner

METHOD FOR DETECTION OF FLOW OBSTRUCTION IN AN EXTRACORPOREAL CIRCUIT, APPARATUS AND COMPUTER PROGRAM

PRIORITY CLAIM

The present application is a National Phase of International Application No. PCT/EP2019/070582, filed Jul. 31, 2019, which claims priority to Swedish Application No. 1850967-9, filed Aug. 9, 2018. The entire contents of each application are incorporated herein by reference and relied upon.

The present application relates to detection of flow obstruction. More specifically, it relates to detection of flow obstruction in extracorporeal blood circuits by analyzing pressure signals. The invention also provides an apparatus in which the method has been implemented, as well as a computer program product that is useful in connection with said detection.

TECHNICAL BACKGROUND

In extracorporeal blood treatment, blood is taken out of a patient, treated and then reintroduced into the patient by means of an extracorporeal flow circuit. Generally, the blood is circulated through the circuit by one or more pumping devices. The circuit is connected to a blood vessel access of the patient, typically via one or more access devices, such as needles or catheters, which are inserted into the blood vessel access. Such extracorporeal blood treatments include hemodialysis, hemodiafiltration, hemofiltration, plasmapheresis, etc.

In extracorporeal blood treatment, it is vital to minimize the risk for malfunctions in the extracorporeal blood flow circuit, since these may lead to a potential life-threatening condition of the patient. Serious conditions may arise if the extracorporeal blood flow circuit is disrupted. Furthermore, the patient's blood as such is also quite sensitive as it contains fragile cells and complex biological structures. If blood is exposed to a harsh environment, there is a risk that these cells and biological structures will be harmed and that hemolysis will occur.

Several risk factors for hemolysis are known. The water from the water supply may contain harmful chlorine or chloramines. These compounds may be removed by carbon filtration. It is important to check incoming water and remove all harmful substances before using the water in medical treatments. Other chemical compounds that may cause hemolysis could be components of disinfection compositions. Examples of such compounds are formaldehyde, chlorine or peracetic acid. It is important to include a careful rinsing step in disinfection procedures involving potentially dangerous chemicals. High temperatures may also harm the blood. It is common to disinfect medical equipment by raising the temperature. High temperatures could also be obtained accidentally when running an extracorporeal blood treatment. It is therefore important to continuously monitor the dialysate temperature in order to minimize the risk for hemolysis. The chemical composition of the dialysate liquid is also an important risk factor. Most dialysate liquids are obtained locally by mixing concentrates with water. It is essential to ensure that dialysate composition is correct. Finally, an important risk factor for hemolysis is mechanical damage. Blood could be mechanically damaged in peristaltic pumps or by kinking of blood lines. Such mechanical damages have been prevented by preventive maintenance of dialysis machines and by checking occlusion of peristaltic blood pump rollers on a regular basis.

As hemolysis, together with extracorporeal blood treatment could be harmful for the patient, there is always a need for monitoring systems and for alarms indicating when the patient is at risk. Such monitoring systems and alarms may be applicable to the hemolysis risk factors that have been discussed above, but also to other, up to now unknown risk factors.

WO2017/156193 A1 discloses methods and systems for detecting an occlusion in a blood circuit of a dialysis system. The dialysis system of this document comprises a specific and complex manifold having, among all, a pressure sensor arranged between the blood pump and the blood filter. The occlusion detection method is based on monitoring pressure measured at that sensor. Furthermore, nothing is disclosed regarding hemolysis and detection of risks for hemolysis.

US2002/0174721 A1 describes a method and a device for detecting stenosis in a tubular line system. To detect stenosis, the frequency spectrum of the pressure signal from the blood pump measured by the venous pressure sensor is analyzed by Fourier transformation. The method is based on the principle that, in response to the existence of a stenosis, the dynamic performance of the tubular line system changes so that the higher frequency components of the pressure signal generated by the blood pump are attenuated.

SUMMARY OF THE INVENTION

In a first aspect, the present invention relates to an extracorporeal circulation blood or treatment device comprising:
  a filter having a blood compartment and a dialysate compartment separated by a semipermeable membrane, said blood compartment having an inlet and an outlet, and said dialysate compartment having an inlet and an outlet;
  an arterial blood line adapted for transporting blood from the patient (P) to the inlet of the blood compartment of the filter, having an arterial connection adapted for being connected to a patient, a peristaltic arterial blood pump and an arterial pressure sensor located between the arterial connection and the arterial blood pump;
  a venous blood line adapted for returning blood from the blood compartment of the filter, having a venous connection adapted for being connected to the patient;
  a dialysate line for forwarding dialysate liquid from a dialysate source to the inlet of the dialysate compartment of the filter;
  a spent dialysate line for removing spent dialysate from the outlet of the dialysate compartment of the filter; and
  a controller, wherein said controller is connected to the arterial blood pump and the arterial pressor sensor, and wherein said controller is set up to receive signals from said arterial pressure sensor when the blood pump is running,
  wherein the controller is set up to determine amplitude variation and frequency of the pressure signals received from the arterial pressure sensor, calculate a parameter value based on said amplitude variation and said frequency, and issue an alarm if the parameter value exceeds a pre-set threshold value.

In a preferred embodiment, the controller continuously determines the variance of amplitude change of the pressure signals received from the arterial pressure sensor, and that said continuously determined variance is taken into account for calculating said parameter value.

In a preferred embodiment, the venous blood line comprises at least one of:
a) a venous pressure sensor;
b) a venous drip chamber containing a level detector; and
c) a priming detector, each present such sensor or detector sending information to said controller, said information being taken into account for calculating said parameter value.

In a preferred embodiment, the spent dialysate line comprises a pressure sensor and that there is ultrafiltration-measuring cell measuring the liquid flows through the dialysate line and the spent dialysate line, said sensor and said cell sending information to said controller, said information being taken into account when calculating said parameter value.

In a preferred embodiment, the controller is set up to determine if the frequency of the pressure signals from the arterial pressure sensor is the same as the occlusion frequency of the peristaltic arterial blood pump, and where this determination is taken into account when determining said parameter value.

In a second aspect, the invention provides a method for determining occlusions in blood lines mounted on an extracorporeal blood or treatment device, said device having:
- a filter having a blood compartment and a dialysate compartment separated by a semipermeable membrane, said blood compartment having an inlet and an outlet, and said dialysate compartment having an inlet and an outlet;
- an arterial blood line adapted for transporting blood from the patient to the inlet of the blood compartment of the filter, having an arterial connection adapted for being connected to a patient, a peristaltic arterial blood pump and an arterial pressor sensor located between the arterial connection and the arterial blood pump;
- a venous blood line adapted for returning blood from the blood compartment of the filter, having a venous connection adapted for being connected to the patient
- a dialysate line for forwarding dialysate liquid from a dialysate source to the inlet of the dialysate compartment of the filter;
- a spent dialysate line for removing spent dialysate from the outlet of the dialysate compartment of the filter; and
- a controller, wherein said controller is connected to the arterial blood pump and the arterial pressor sensor, and wherein said controller is set up to receive signals from said arterial pressure sensor when the blood pump is running, comprising the steps of
a) receiving pressure signals from said arterial pressure sensor;
b) continuously determining amplitude variation and frequency of the pressure signals received in step a);
c) calculating a parameter value based on said amplitude variation and said frequency; and
d) issuing an alarm if the parameter value exceeds a pre-set threshold value.

In a preferred embodiment, the variance of the amplitude variation is determined based on the amplitude variation and frequency continuously measured in step b), and that the variance is taken into account when calculating said parameter value.

In a preferred embodiment, information from at least one of:
a) a venous pressure sensor;
b) a level detector located in a venous drip chamber; and
c) a priming detector is taken into account when calculating said parameter value.

In a preferred embodiment, pressure signals from a pressure sensor of a spent dialysate line and an ultrafiltration measuring cell are taken into account when calculating said parameter value.

In a preferred embodiment, the occlusion frequency of the peristaltic pump is compared with the frequency of the pressure signals from the arterial pressure sensor, and this comparison is taken into account when determining said parameter value.

In a third aspect, the present invention provides a computer program product, which when implemented in a controller of an extracorporeal circulation blood or treatment device enables said controller to carry out the method of the second aspect.

DETAILED DESCRIPTION OF THE INVENTION

The present invention relates to a method of detecting occlusions, such as kinks in an extracorporeal blood circuit. In particular, the method is particularly suited for detecting kinks in the part of the arterial blood line between the arterial peristaltic blood pump and the blood chamber of the blood filter.

The present invention will now be described with reference to the enclosed drawings in which:

FIG. 2 illustrates occlusion of the blood pump segment of the arterial bloodline of the extracorporeal blood circuit.

Figure 1:
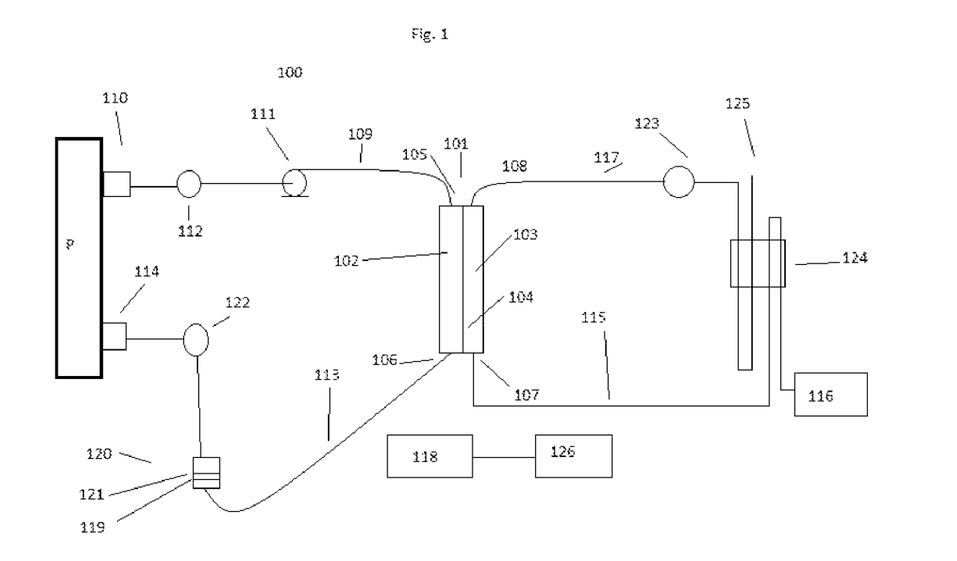
FIG. 1 schematically discloses an example of an extracorporeal blood or treatment device on which the method for determining occlusions according to the present invention has been implemented.

The extracorporeal blood or treatment device 100, disclosed in FIG. 1, comprises a filter 101 having a blood compartment 102 and a dialysate compartment 103. These compartments are separated by a semipermeable membrane 104. An arterial blood line 109 is connected to the vascular system of a patient P by a connection 110, typically an arterial needle and suitable connection means. The blood then passes an arterial pressure sensor 112 on its way to the blood pump 111. The blood pump 111 forwards the blood to the inlet 105 of the blood compartment 102 of the blood filter 101. In the blood compartment 102, the blood is dialyzed over the semipermeable membrane 104 against dialysate liquid in the dialysate compartment 103. The blood then continues through the outlet 106 of the blood compartment 102 to the venous blood line 113 and passes through a venous drip chamber 120 including a level detector 121 and a venous pressor sensor 119, and finally a priming detector 122 until it reaches the venous connection 114, typically a venous needle and suitable connection means.

The dialysate liquid is transported from a dialysate source 116 through a dialysate line 115 to the inlet 107 of the dialysate compartment of the blood filter 101. The dialysate source 116 could be a dialysate preparation device where dialysate liquid prepared by mixing concentrates with water. Alternatively, the dialysate source 116 could be a bag containing ready-to-use dialysate liquid. The spent dialysate leaves the dialysate compartment 103 through outlet 108 and continues through the spent dialysate line 117. There is a pressure sensor 123 along the spent dialysate line 117. Furthermore, there is an ultrafiltration measuring cell 124 set up to measure the liquid flows throw the dialysate line 115 and the spent dialysate line 117. The spent dialysate line ends at a drain 125.

The extracorporeal blood or treatment device 100 also comprises a controller 118 for controlling and supervising the device. Specifically, the arterial blood sensor 112 and the peristaltic arterial blood pump 111 are connected to the controller 118 and are typically continuously transferring data to it. Other parts of the device 100 that also may send data to the controller 118 are venous pressure sensor 119, the level detector 121 of the venous drip chamber 120, priming detector 122, spent dialysate line pressure sensor 123, and the ultrafiltration measuring cell 124. The controller is set up to initiate alarms from alarm means 126 under certain conditions.

When detecting flow obstructions such as kinks in the part of the arterial blood line 109 between the arterial peristaltic blood pump 111 and inlet 105 to the blood compartment 102 of the blood filter 101, it turns out to be important to monitor the pressure detected by the arterial pressure sensor 112.

In principle, all hemodialysis machines currently in the market have a peristaltic pump to pump the blood through the blood lines. The arterial pressure that is measured in front of the pump, that is, by the arterial pressure sensor 112, is normally within the range of −50 to −200 mm Hg and the negative pressure is caused by the blood pump sucking the blood through the needle and pumping the blood through the blood filter 101 and back again to the patient P through the venous blood line 113.

The working principle of a peristaltic pump is to forward liquid in a segment of a tube (the pump segment) by occluding the tube and pushing forward. This is typically carried out by arranging spring-loaded rollers on the periphery of a rotating wheel and letting said rollers press on the pump segment.

It is important to have the right occlusion of the pump segment in order to obtain correct and predictable blood flow rates, especially if blood flow is determined based on the rotational speed of the pump wheel.

Figure 2A:
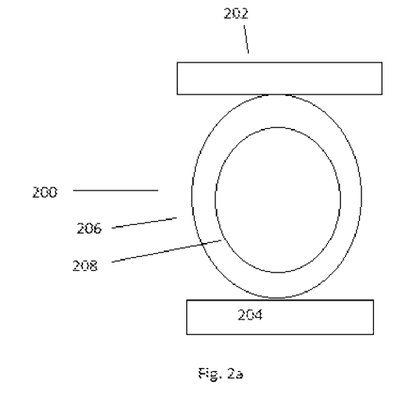
FIG. 2a shows a non-occluded segment and FIG. 2b discloses a fully occluded segment.

FIG. 2a discloses a completely non-occluded pump segment 200. Typically, a pump segment 200 has a wall thickness between the outer wall 206 and the inner wall 208 of about 2 mm, an inner diameter of about 8 mm and an outer diameter of about 12 mm. The pump segment 200 is arranged between a pump track 202 and a pump roller 204.

Figure 2B:
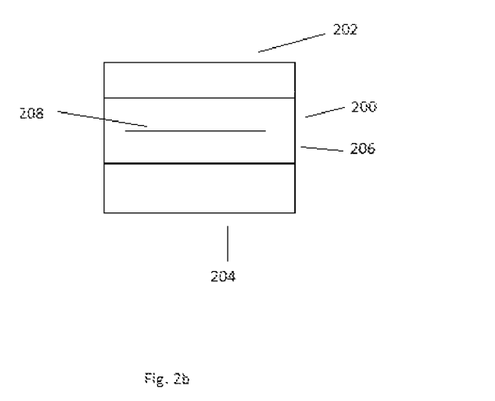

FIG. 2b shows a fully occluded pump segment 200, which is an ideal situation. Here, the pump segment 200 is occluded but the walls are not deformed. Accordingly, the thickness of the occluded segment 200 is double the wall thickness. If the wall thickness is 2 mm, the thickness of the occluded segment 200 would be 4 mm.

However, in practice, and in order to ensure that the pump segment 200 always is occluded on operation, the spring-loaded blood pump rollers 204 press harder. The pump segment 200 is therefore normally over-occluded. Typically, the pump segment walls are flattened to about 70% of the original thickness. In the following, the distance between a blood pump roller 204 and the pump track 202 (that distance is filled by the occluded blood pump segment 200) is referred to as the occlusion.

Figure 3:
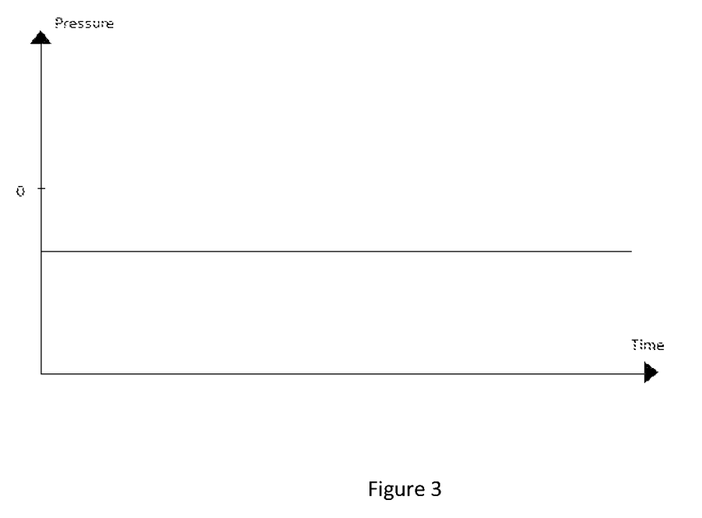
FIG. 3 discloses pressure signals from the arterial pressure sensor of an extracorporeal blood circuit during treatment of a patient in a situation where there is no occlusion in the arterial blood line between the arterial peristaltic blood pump and the blood filter.
Figure 4:
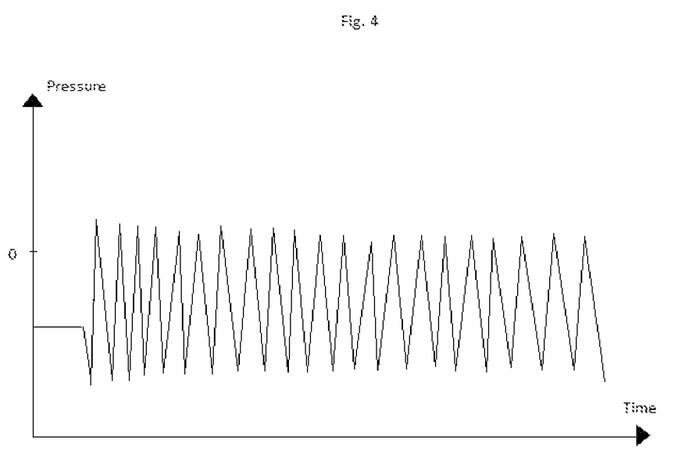
FIG. 4 shows pressure signals from the arterial pressure sensor of an extracorporeal blood circuit during treatment of a patient in a situation where there is an occlusion, such as a kink, in the arterial blood line between the arterial peristaltic pump and the blood filter.

A diagram of arterial pressure over time measured by the arterial pressure sensor 112 located on the suction side of arterial blood pump 111 are shown in FIGS. 3 and 4. FIG. 3 shows a curve representing a normal treatment. The arterial pressure is negative and stable. The occlusion of the blood pump segment 200 is normal and there are no kinks on the blood line. The blood is stably forwarded from the suction side to the pressure side.

If the occlusion of the pump segment 200 is incorrect or the blood pump 111 for any other reason cannot be occluded properly, there might be a back flow in the blood pump 111 when the rollers 204 engage or disengage. FIG. 4 shows an oscillating arterial pressure caused by back flow in the blood pump 111. The effective blood flow rate is reduced and the red blood cells may be damaged and hemolysis occurs.

There is another situation where backflow may occur, and that is when there is a kink on the blood line 109 after the peristaltic arterial blood pump 111 and before the blood filter 101. Such a kink may lead to counter pressures as high as >1000 mm Hg. These high counter pressures and the associated backflow are dangerous to blood cells and may lead to hemolysis.

The present invention therefore aims at detecting this oscillating pressure by determining frequency and amplitude. As the oscillation is caused by backflow in the blood pump, its frequency must be the oscillation frequency, which is an integer multiple of the pump speed expressed as revolutions per minute. Furthermore, a large pressure amplitude is associated with a higher risk for hemolysis than a low amplitude. The controller 118 is set up to continuously monitor these two parameters and determines a parameter value based up on the outcome. In case the frequency value could be regarded as an integer multiple of the pump speed, and the pressure amplitude exceeds a threshold value, the control parameter is assigned a value indicating alarm conditions. An alarm may be issued by alarm means 126 and the blood pump 111 may be stopped.

Figure 5:
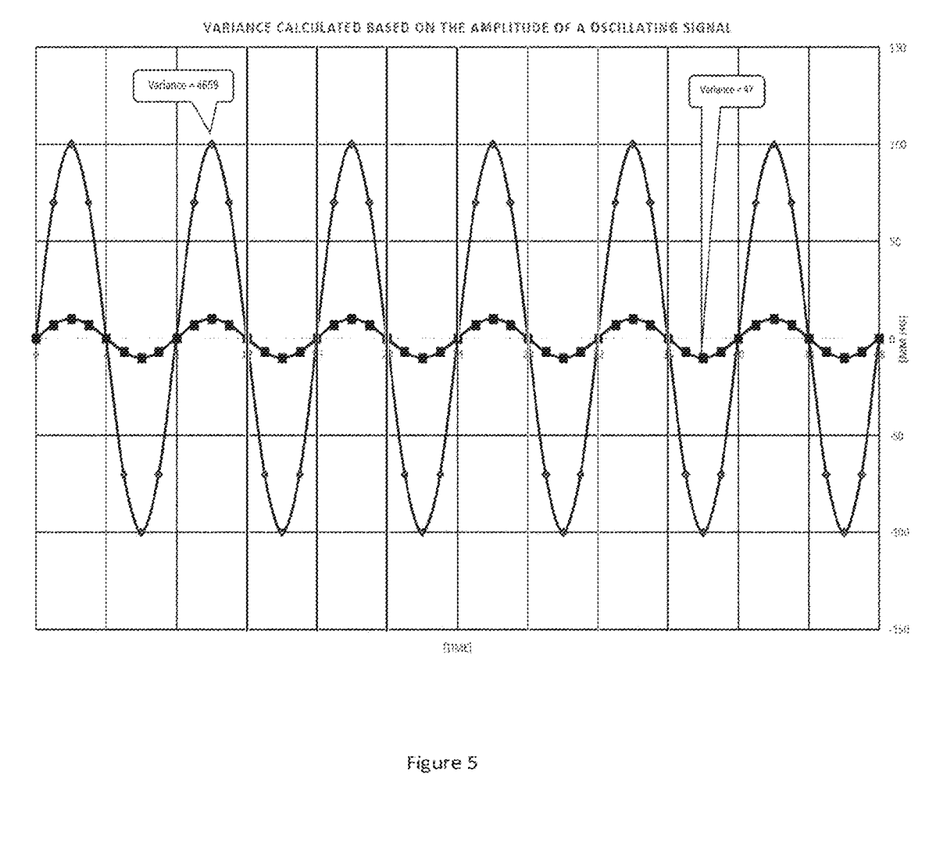
FIG. 5 illustrates the detection of an oscillating signal by determining the variance.

In a preferred embodiment, the controller 118 continuously determines the variance of the amplitude of the pressure for a time segment of specific length. In case the variance is higher than a pre-set threshold value, the controller may issue an alarm and the blood pump 111 may be stopped. FIG. 5 shows oscillating pressure signals approximated as sinus curves. The brighter curve has a maximum amplitude of 20 mm Hg, whereas the darker curve has a maximum amplitude of 200 mm Hg. The frequencies of the two curves are the same and correspond to a typical blood pump frequency. The variance of the brighter low-amplitude curve amounts to 47, and the variance of darker high-amplitude curve amounts to as much as 4659. Accordingly, calculating the variance value renders it easier to differentiate between meaningful signals and noise. Moreover, the variance value is not dependent of the average signal level. The value is the same irrespective of whether the average level is zero, or above or below that level.

The controller 118 may rely upon more data when assessing alarm conditions. In case of incorrect occlusion or kinks, the data from at least pressure sensor 119 will differ from expected levels. For instance, in case of an obstruction of the blood line, the venous pressure sensor 119 will detect a pressure that is below what could have been expected.

Similarly, data from pressure sensor 123 and ultrafiltration measuring cell 124 may also diverge from expected levels. Such extra data may further support and increase reliability of the monitoring process. Additionally, if clearance measurements are made on-line, a reduction of clearance or an abnormally low blood flow rate to clearance ratio could indicate a reduced effective blood flow rate caused by an obstruction in the blood line.

The invention claimed is:

1. An extracorporeal circulation blood or treatment device comprising:
    a filter having a blood compartment and a dialysate compartment separated by a semipermeable membrane, said blood compartment having an inlet and an outlet, and said dialysate compartment having an inlet and an outlet;
    an arterial blood line adapted for transporting blood from a patient to the inlet of the blood compartment of the filter, the arterial blood line having an arterial connection adapted for being connected to the patient, a peristaltic arterial blood pump and an arterial pressure sensor located between the arterial connection and the peristaltic arterial blood pump;
    a venous blood line adapted for returning blood to the patient from the blood compartment of the filter, the venous blood line having a venous connection adapted for being connected to the patient;
    a dialysate line for forwarding dialysate liquid from a dialysate source to the inlet of the dialysate compartment of the filter;
    a spent dialysate line for removing spent dialysate from the outlet of the dialysate compartment of the filter; and
    a controller in operable communication with the peristaltic arterial blood pump and the arterial pressure sensor, wherein said controller is configured to receive pressure signals from said arterial pressure sensor when the peristaltic arterial blood pump is running,
    wherein the controller is configured to:
        determine an amplitude variation and a frequency of the pressure signals received from the arterial pressure sensor,
        determine or receive an indication of an occlusion frequency of the peristaltic arterial blood pump during a pumping operation of the peristaltic arterial blood pump,
        determine a difference or an integer multiple between the frequency of the pressure signals from the arterial pressure sensor and the occlusion frequency of the peristaltic arterial blood pump,
        calculate a parameter value based on (i) said amplitude variation and (ii) the difference or the integer multiple between the frequency of the pressure signals and the occlusion frequency, and
        issue an alarm when the parameter value exceeds a pre-set threshold value.

2. The extracorporeal circulation blood or treatment device according to claim 1, wherein the venous blood line includes at least one of a venous pressure sensor, a venous drip chamber containing a level detector, and a priming detector,
    wherein each included sensor or detector is configured to send information to said controller, and
    wherein calculating said parameter value is further based on said information.

3. The extracorporeal circulation blood or treatment device according to claim 1, wherein the spent dialysate line comprises a pressure sensor and an ultrafiltration-measuring cell, the ultrafiltration-measuring cell configured to measure the dialysate liquid flowing through the dialysate line and the spent dialysate flowing through the spent dialysate line, wherein said pressure sensor and said ultrafiltration-measuring cell are each configured to send information to said controller, and wherein calculating said parameter value is further based on said information.

4. The extracorporeal circulation blood or treatment device according to claim 1, wherein the controller is configured to continuously determine the amplitude variation and the frequency of the pressure signals received from the arterial pressure sensor.

5. A method for determining occlusions in blood lines mounted on an extracorporeal blood or treatment device, said extracorporeal blood or treatment device including:
    a filter having a blood compartment and a dialysate compartment separated by a semipermeable membrane, said blood compartment including an inlet and an outlet, and said dialysate compartment including an inlet and an outlet;
    an arterial blood line adapted for transporting blood from a patient to the inlet of the blood compartment of the filter, the arterial blood line having an arterial connection adapted for being connected to the patient, a peristaltic arterial blood pump, and an arterial pressure sensor located between the arterial connection and the peristaltic arterial blood pump;
    a venous blood line adapted for returning blood to the patient from the blood compartment of the filter, the venous blood line having a venous connection adapted for being connected to the patient;
    a dialysate line for forwarding dialysate liquid from a dialysate source to the inlet of the dialysate compartment of the filter;
    a spent dialysate line for removing spent dialysate from the outlet of the dialysate compartment of the filter; and
    a controller in operable communication with the peristaltic arterial blood pump and the arterial pressure sensor, wherein said controller is configured to receive signals from said arterial pressure sensor when the peristaltic arterial blood pump is running,
    the method comprising:
        receiving pressure signals from said arterial pressure sensor;
        determining an amplitude variation and a frequency of the pressure signals received from said arterial pressure sensor;
        determining or receiving an indication of an occlusion frequency of the peristaltic arterial blood pump during a pumping operation of the peristaltic arterial blood pump;
        determining a difference or an integer multiple between the occlusion frequency of the peristaltic arterial blood pump and the frequency of the pressure signals from the arterial pressure sensor;
        calculating a parameter value based on said amplitude variation and the difference or the integer multiple between the occlusion frequency of the peristaltic arterial blood pump and the frequency of the pressure signals; and
        issuing an alarm when the parameter value exceeds a pre-set threshold value.

6. The method according to claim 5, wherein calculating said parameter value is further based on information from at least one of a venous pressure sensor, a level detector located in a venous drip chamber, and a priming detector.

7. The method according to claim 5, wherein calculating said parameter value is further based on pressure signals from a pressure sensor of a spent dialysate line and an ultrafiltration measuring cell.

8. The method according to claim 5, further comprising continuously determining the amplitude variation and the frequency of the pressure signals received from said arterial pressure sensor.

9. A non-transitory, computer-readable medium storing instructions, which when executed by a processor of an extracorporeal circulation blood or treatment device, cause the processor to:
receive pressure signals from an arterial pressure sensor;
determine an amplitude variation and a frequency of the pressure signals received from the arterial pressure sensor;
determine or receive an indication of an occlusion frequency of a peristaltic pump during a pumping operation of the peristaltic pump;
determine a difference or an integer multiple between the occlusion frequency of the peristaltic pump and the frequency of the pressure signals received from the arterial pressure sensor;
calculate a parameter value based on said amplitude variation and the difference or the integer multiple between the occlusion frequency of the peristaltic pump and the frequency of the pressure signals; and
issue an alarm when the parameter value exceeds a pre-set threshold value.

10. The non-transitory, computer-readable medium of claim 9, wherein the processor is configured to continuously determine the amplitude variation and the frequency of the pressure signals received from the arterial pressure sensor.

* * * * *